United States Patent [19]
Hershfield et al.

[11] Patent Number: 5,648,216
[45] Date of Patent: Jul. 15, 1997

[54] METHOD FOR IDENTIFYING CANINE CHROMOSOMES

[75] Inventors: Bennett Hershfield, Ithaca, N.Y.; Daniel Goldowitz, Memphis, Tenn.

[73] Assignee: Cornell Research Foundation, Inc., Ithaca, N.Y.

[21] Appl. No.: 410,977

[22] Filed: Mar. 27, 1995

[51] Int. Cl.$^6$ .............................. C12Q 1/68; C07H 21/04
[52] U.S. Cl. ...................... 435/6; 536/24.3; 536/24.31
[58] Field of Search ............................ 435/6; 536/24.31, 536/24.3

[56] References Cited

U.S. PATENT DOCUMENTS

| | | | |
|---|---|---|---|
| 5,041,733 | 8/1991 | Noguchi et al. | 250/461.2 |
| 5,138,170 | 8/1992 | Noguchi et al. | 250/461.2 |

FOREIGN PATENT DOCUMENTS

WO93/06245  4/1993  WIPO .

OTHER PUBLICATIONS

Yasue, H. et al., Cell Struct Funct 16:475-479 (1991).
Fanning, T.G. et al., Cytogenet Cell Genet 48:214-219 (1988).
Modi, W.S. et al., Gene Analyt Technol 4:75-85 (1987).
Rothuizen, J. et al., Theoretical and Applied Genetics 89:403-406 (1994).
Stone, D.M. et al., Genome 34:407-412 (1991).
Lin, C.C. et al., Chromosoma 101:19-24 (1991).
Selden, J.R. et al., Cytogenet Cell Genet 15:380-387 (1975).
Modi, W.S. et al., Cytogenet Cell Genet 48:208-213 (1988).
Minnick, M.F. et al., Gene 110:235-238 (1992).
Wayne, R.K. et al., Cytogenet Cell Genet 44:123-133 (1987).
Rajcan-Separovic, E. et al., Genome 36:984-985 (1993).
Katzir, N. et al., Proc Natl Acad Sci USA 82:1054-1058 (1985).
Amariglio, E.M. et al., Proc Natl Acad Sci USA 88:8136-8139 (1991).
Pathak, S. et al., Cytogenet Cell Genet 34:112-118 (1982).
Hershfield, B. et al., Chromosoma 99:125-130 (1990).
Hershfield, B. et al., J. Hered 82:251-254 (1991).
Hershfield, B. et al., Anim Genet 24:293-295 (1993).
Hino, O. et al., Proc Natl Acad Sci USA 90:730-734 (1993).
Manolache, M. et al., Can J Genet Cytol 18:513-518 (1976).
Ostrander E.A. et al., Genomics 16:207-213 (1993).
Wayne, R.K. et al., Cytogenet Cell Genet 44:123-133 (1987a).
Fan, Y.S. et al., Proc Natl Acad Sci USA 87:6223-6227 (1990).
Matthews et al. Analytical Biochemistry 169: pp. 1-25 (1988).
Boyle et al. PNAS 87: pp. 7757-7761 (1990).

*Primary Examiner*—Stephanie W. Zitomer
*Assistant Examiner*—Ethan Whisenant
*Attorney, Agent, or Firm*—Nixon, Hargrave, Devans & Doyle

[57] ABSTRACT

The present invention is directed to an isolated oligonucleotide having a nucleotide sequence which includes a sequence corresponding to SEQ ID NO:1, or which includes a sequence complementary to the sequence corresponding to SEQ ID NO:1. Methods for differentiating and/or identifying canine chromosomes using the isolated oligonucleotide are also provided. The invention further provides a method for differentiating and/or identifying canine chromosomes using a labeled repetitive probe, wherein the labeled repetitive probe is hybridized to canine chromosomes and the resulting hybrids are detected fluorescently. In one embodiment, the DNA sequence of the repetitive probe is provided in the recombinant plasmid designated pCfBE013/BH.

21 Claims, 1 Drawing Sheet

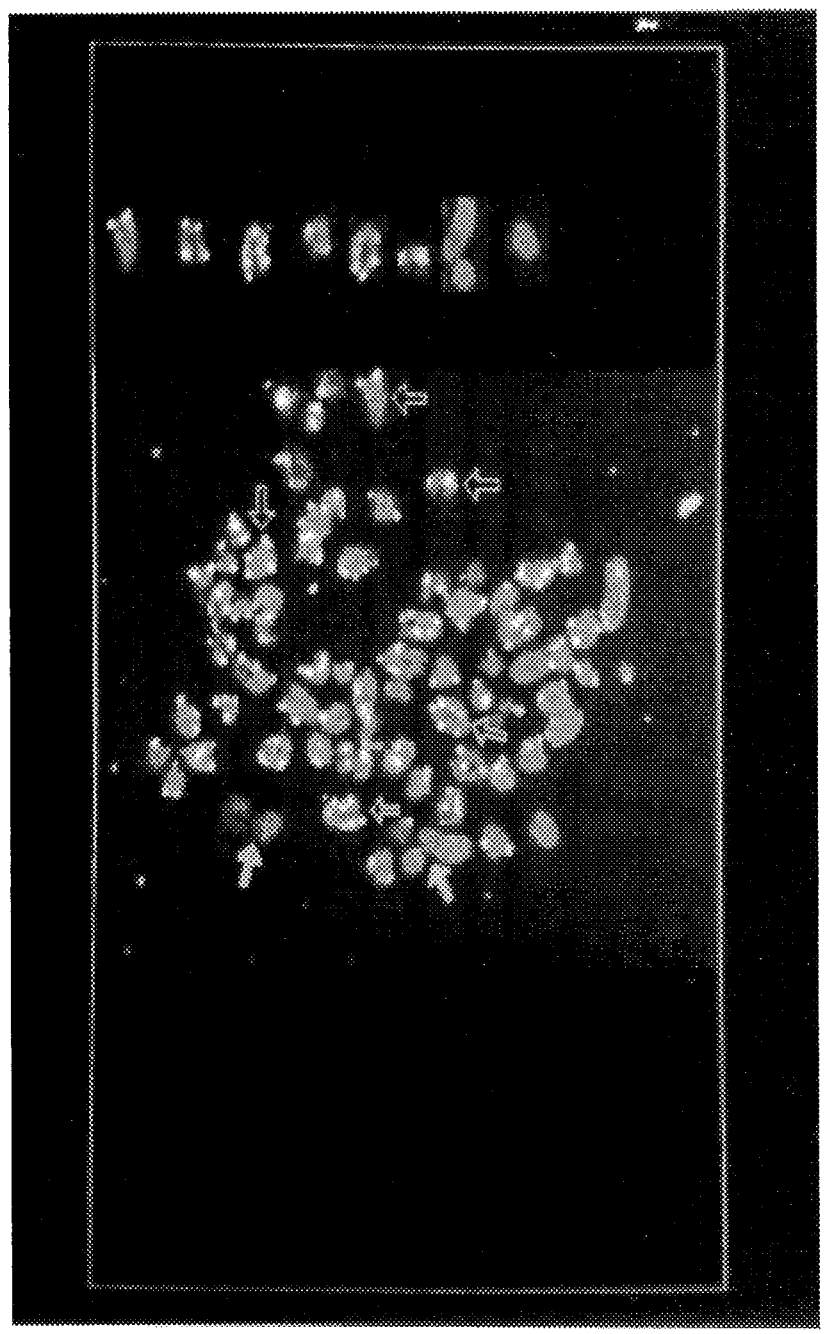

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 737 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Canis familiaris
        ( B ) STRAIN: beagle ( v i i ) IMMEDIATE SOURCE:
        ( A ) LIBRARY: canine polymorphic sequences pBR322 minilibrary - Hershfield
        ( B ) CLONE: pCfBE013/BH ( x i ) SEQUENCE DESCRIPTION: SEQ ID NO:1:

```
GGTCTGGTGG CCAGTGGAAT GGCGCTTGCT CCGGCCAGAG CGCGATCCTG GAAACCCAGG    60

ATCGAGTCCC ATGTCGGGCT CCCGGTGCAT GGAGCCTGCT TCTCCCTCTG CCTGTGTCTG   120

TGCCTCTCTC TCTCTCTCTC TCTGTGACTA TCATAAAAAA ATATATATAT ATTTCTGTAT   180

CCCCAGTCTT AGCCCAGTGC CTGCTAGGAA GTGTGAGTTA ACAAACATTT GTGACTGACT   240

GACCAACTAG ATGGATGAAT CCCTATTCCC AGTGTGCACA GCCAAGATAA TATTATTTAC   300

TGGTGGCTCA AGTGAGCACC CAGGAACTCC TGTAAATACT TCACGAGCAT CATTTTCCTC   360

TTTGATCCTT CATGATCCAC CCAGTGAGAG AGGTGCTACC AGTCTCCCCC TCTTGAGGAG   420

GGACACTGCC GAGGACACAG AAGGAGGTTA GGAGAATGCC TGTGGTCTTA CTGCCACTTA   480

GCAGCAGTGT GGGAAGAGGA CCTGGGATGG GGAGGCGGGG CGGTCGGTCG CATGCTGGCG   540

CCCACTTGCC TAGGCACCCT TCCACAATGC CTGGCTACCC CGAGCTTGGA CGATGTGGCT   600

GCTGAATGGG TCCAAGCACT GATGGCTGCC TGGACTGCAC AACCTTTAGG TCACTGAGGA   660

TCTTTTCTGT TCCAGTCCAG TCCAGCCCTA GCAGCTTCTG CCAGGAACCT GGACGAGGAG   720

GTGGGGAGGT GGGATCC                                                  737
```

METHOD FOR IDENTIFYING CANINE CHROMOSOMES

This invention was made with support from the United States Government (National Eye Institute of the National Institute of Health Grant No. EY09586).

FIELD OF THE INVENTION

The present invention relates to a canine interspersed middle repetitive probe designated pCfBE013/BH, and to methods for differentiating and/or identifying canine chromosomes using a repetitive probe.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The diploid chromosome complement of the domestic dog Canis familiaris consists of 76 acrocentric autosomes and an X-Y sex chromosome pair (Selden et al., 1975). The autosomes, in addition to being numerous, are fairly small and resemble each other even after G-banding. The technical difficulties of working on the canine autosomes due to their small size, combined with the evolutionary history of the canine karyotype as a highly derived version of the primitive carnivore karyotype (probably as a result of Robertsonian fusions—Wayne et al., 1987b), have resulted in an almost complete lack of knowledge about the comparative cytogenetics of the dog. Efforts to perform positional cloning of mutations using canine models of gene defects are seriously hampered without a knowledge of chromosomal synteny relationships between the dog and species with detailed chromosomal maps (such as man and mouse).

Previous techniques in which marking of canine autosomes have been attempted include G-banding, in situ hybridization of highly repetitive DNAs, C-banding, N-banding, and Q-banding.

Because of the small size and numerous amount of canine autosomes, two studies on the G-banded karyotype of the dog differed on the banding patterns and numbering systems for several of the autosomes (Selden et al., 1975; Manolache et al., 1976). Later reports attempted to resolve some of the inconsistencies by relying upon G-banded karyotypes from sequentially stained amethopterin synchronized lymphocyte cultures (Stone et al., 1991) or by using fibroblast cell lines of the grey wolf Canis lupus (a species with a completely homologous karyotype to the domestic dog—Wayne et al., 1987a).

The in situ hybridization studies that have been carried out on canine autosomes have been limited in scope to grain count statistics on the binding of canine satellite DNAs to the centromeric heterochromatin (Modi et al., 1988).

C-banding of the centromeric heterochromatin labels only 7 or 8 unspecified autosomes, while N-banding (silver staining indicative of nucleolar organizer regions) marked three pairs of autosomes and the Y chromosome (Pathak et al., 1982; Stone et al., 1991). Q-banding resulted in fluorescing regions which corresponded to darkly staining G-band regions, but the resolution was minimal (Stone et al., 1991).

Despite these various attempts to mark canine autosomes for identification and/or differentiation, the problems associated with the small size and numerous amounts of the canine autosomes has still hampered the development of an accurate and reproducible method for identification and/or differentiation thereof.

The development of identification methods for the canine autosomes that will permit rapid and unequivocal recognition of chromosome groups is an important first step in the comparative mapping of the canine genome. Further, these methods will ideally be capable of being applied simultaneously with the in situ hybridization of unique copy euchromatic chromosomal probes of interest from dog or other species (such as man or mouse).

In mammalian species other than man and mouse, the usefulness of the different types of repetitive probes for chromosome banding and recognition studies is difficult to predict. For example, fluorescent in situ hybridizations of Alu-like sequences to chromosome sets from pig, sheep, and cow were found to produce indistinct and diffuse hybridization patterns that were not useful for chromosome recognition (Yasue et al., 1991; Rajcan-Separovic and Sabour, 1993). By contrast, the highly repetitive C5 satellite probe from the Chinese muntjac which was found to hybridize to the centromeric heterochromatin of the Chinese muntjac and the Indian muntjac was shown to also bind to a limited number (ca. 30) of interstitial sites on the arms of only the Indian muntjac chromosomes (Lin et al., 1991).

For the dog, previous work on interspersed repetitive DNAs has been limited to the identification of a LINE element homologous to the Kpn repeat of primates (Katzir et al., 1985; Amariglio et al., 1991) and the canid-specific SINE element (Minnick et al., 1992).

It should be apparent from the above discussion that the accuracy of particular chromosome marking methods can vary between species. A successful G-banding in one species, or a successful FISH technique in a species, does not indicate that G-banding and/or FISH techniques will be successful in identifying and/or differentiating chromosomes from another different species. In view of the problems encountered in marking canine chromosomes, despite some success in marking chromosomes from other species, a need continues to exist for an accurate method for differentiating and/or identifying canine chromosomes.

SUMMARY OF INVENTION

To this end, it is an object of the subject invention to provide an accurate and reproducible method for the identification and/or differentiation of canine chromosomes. It is a further object of the invention to provide an oligonucleotide useable as a canine repetitive probe in such methods.

The invention provides an isolated oligonucleotide having a nucleotide sequence which includes a sequence corresponding to SEQ ID NO:1, or which includes a sequence complementary to the sequence corresponding to SEQ ID NO:1. Methods for differentiating and/or identifying canine chromosomes using the isolated oligonucleotide are also provided.

The invention further provides a method for differentiating and/or identifying canine chromosomes using a labeled repetitive probe, wherein the labeled repetitive probe is hybridized to canine chromosomes and the resulting hybrids are detected fluorescently.

The invention further provides a recombinant plasmid designated pCfBE013/BH, deposited with the A.T.C.C. on Mar. 24, 1995 under Accession No. 69770. Further provided is an isolated BamHI restriction fragment from this recombinant plasmid pCfBE013/BE.

BRIEF DESCRIPTION OF THE DRAWINGS

These and other features and advantages of this invention will be evident from the following detailed description of preferred embodiments when read in conjunction with the accompanying drawing in which:

FIG. 1 illustrates the fluorescent in situ hybridization of pCfBE013/BH to canine chromosomes. Yellow-green fluorescence indicates positive signal. Every afrowed chromosome is duplicated at higher magnification in cutout form (to the right) and represents a reproducible pattern of hybridization illustrated in this spread. Open arrows=hybridizing chromosomes, closed arrows=nonhybridizing chromosomes.

DETAILED DESCRIPTION

A chromosome characteristically contains regions which have DNA sequences that contain DNA repeated segments. The term "repeated" has reference to the fact that a particular DNA segment occurs a plurality (i.e., at least two) of times as the same DNA sequence. Two general classes of repeated (also known as repetitive) sequences occur in eukaryotic genomes. The first is arranged in multiple tandem repeats and is referred to as satellite DNA. Satellite DNAs are located in chromosome centromeric regions. The second type of repetitive element is referred to as interspersed repetitive sequences, which are usually scattered throughout chromosomal DNA. These interspersed sequences are further divided based on size into short interspersed sequences (SINES) and long interspersed sequences (LINES).

As discussed more fully below, the method of the subject invention relies on the ability of a probe to "differentially hybridize" to canine chromosomes. The probe used in the subject invention is a repetitive probe. This means that the sequence of the probe will hybridize to "repetitive sequences" in the canine genome. Such repetitive sequences are defined above. The invention is based upon the distribution pattern of these repetitive sequences within the canine genome. A particular chromosome or subset of chromosomes will have a characteristic pattern of probe hybridization, indicating characteristic location of the repetitive sequences within that particular chromosome or subset of chromosomes. Therefore, following hybridization of the probe to the canine chromosomes and detection of the hybridization pattern, one can examine the pattern to determine several things. First, identical patterns of hybridization on two different chromosomes will likely indicate that the chromosomes are sister chromosomes, i.e. a pair of chromosomes. Second, having determined the particular hybridization pattern for a given canine chromosome (i.e. the chromosome designated #1), a specimen can be examined for that particular hybridization pattern, thereby identifying a chromosome within a specimen as canine chromosome #1. Accordingly, the hybridization patterns (referred to as hybridization pattern profiles) can be used to differentiate canine chromosomes from one another (i.e. by comparing chromosomes within a single specimen) or to identify canine chromosomes (i.e. by comparing chromosomes within a specimen to a pre-established pattern profile for canine chromosomes).

The term chromosome generally refers to a heredity-bearing gene carrier of a living cell which is derived from chromatin and which comprises DNA and protein components. The term chromosome, as used herein, includes canine autosomes and the "sex" chromosomes, X and Y.

The term probe as used herein refers to an oligonucleotide (i.e. a polynucleotide), or a mixture of oligonucleotides, such as DNA sequence(s) or DNA segment(s) which has (or have) been chemically combined (i.e., associated) with individual label-containing moieties. Each such oligonucleotide of a probe is typically single stranded at the time of hybridization to a target chromosome.

As used herein, a directly labeled probe designates or denotes a nucleic acid probe whose label after hybrid formation with a target is detectable without further reactive processing of hybrid.

An indirectly labeled probe designates or denotes a nucleic acid probe whose label after hybrid formation with a target must be further reacted in subsequent processing with one or more reagents to associate therewith one or more moieties that finally result in a detectable entity.

The term hybrid refers to the product of a hybridization procedure between a probe and a target chromosome. Typically, a hybrid is a molecule that includes a double stranded, helically configured portion comprised of complementarily paired single stranded molecules, such as two DNA molecules, one of which is a target DNA nucleotide sequence, and the other of which is the labeled DNA nucleotide sequence of a probe.

The recombinant plasmid designated pCfBE013/BH has been deposited in the *Escherichia coli* strain designated INValphaF'/pCfBE013/BH pursuant and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 on Mar. 24, 1995 under A.T.C.C. Accession No. 69770. Plasmid pCfBE013/BH was constructed by inserting the DNA encoding the repetitive probe of the subject invention into the BamHI site of plasmid vector pBR322. Therefore, the DNA encoding the repetitive probe of the subject invention can be obtained by cleaving recombinant plasmid pCfBE013/BH with the restriction endonuclease BamHI.

The invention provides an isolated oligonucleotide having a nucleotide sequence which includes a sequence corresponding to SEQ ID NO:1 (deposited with GenBank under Accession No. U17996). As used herein, a nucleotide sequence corresponding to a particular nucleotide sequence is one which is substantially the same nucleotide sequence, or derivatives thereof (such as deletion and hybrid variants thereof). Nucleotide additions, deletions, and/or substitutions, such as those which do not eliminate the capability of the probe to differentially hybridize to canine chromosomes, are within the scope of a nucleotide sequence corresponding to a particular nucleotide sequence.

Since the genome of *Canis familiaris* is double-stranded, the invention further provides an isolated oligonucleotide having a nucleotide sequence which includes a sequence complementary to the sequence corresponding to SEQ ID NO:1. Each of the "sense" and "anti-sense" strands can be DNA or an RNA copy of the DNA. (Note that in claims referring to RNA, any recited sequence would have a U nucleotide in place of any T nucleotide.)

To utilize these isolated oligonucleotides in methods for differentiating and/or identifying canine chromosomes, the oligonucleotides are preferably labeled with a detectable marker. The term label or detectable marker refers in general sense to a moiety, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). The term fluorescent (and equivalent terms) has general reference to the property of a substance (such as a fluorophore) to produce light while it is being acted upon by radiant energy, such as ultraviolet light or x-rays.

It may also be desirable to utilize these oligonucleotides in a composition with at least one other oligonucleotide capable of differentially hybridizing to canine chromosomes.

The nucleotide sequence corresponding to SEQ ID NO:1 encodes a probe which preferentially and differentially hybridizes to canine chromosomes. In accordance with the subject invention, fragments of an isolated oligonucleotide (the oligonucleotide having a nucleotide sequence which includes a sequence corresponding to SEQ ID NO:1 or which includes a sequence complementary to the sequence corresponding to SEQ ID NO:1) are also provided, the fragments also being capable of differentially hybridizing to canine chromosomes. The term fragment indicates generally only a portion of a larger oligonucleotide or probe sequence. An oligonucleotide, for example, can be broken up, or fragmented into, a plurality of fragments. DNA fragments can be formed by various known techniques, including, for example, enzyme treatment, as with restriction enzymes or polymerases, or the like; limited DNase I digestion; limited mung bean nuclease digestion; sonication; shearing DNA in a French press; shearing DNA through a narrow gauge needle; and the like. Suitable resulting fragments according to the subject invention can be identified by determining whether such fragments differentially hybridize to canine chromosomes (which can be done as described herein).

Having provided the oligonucleotides and fragments thereof according to the subject invention, these are used in a method for differentiating canine chromosomes in a specimen. The method comprises:

contacting canine chromosomes in a specimen under hybridizing conditions with a labeled isolated oligonucleotide of the subject invention so as to produce hybrids between said canine chromosomes and the labeled oligonucleotide;

detecting the hybrids by detecting the labeled oligonucleotide present in the hybrids;

determining for each hybrid a profile pattern of hybridization of said labeled oligonucleotide to said canine chromosome; and differentiating said canine chromosomes by comparing said profile pattern of hybridization of each hybrid to profile patterns of the other hybrids.

The invention further provides a method for identifying canine chromosomes in a specimen which comprises:

contacting canine chromosomes in a specimen under hybridizing conditions with a labeled isolated oligonucleotide according to the subject invention so as to produce hybrids between said canine chromosomes and the labeled oligonucleotide;

detecting the hybrids by detecting the labeled oligonucleotide present in the hybrids;

determining for each hybrid a profile pattern of hybridization of said labeled oligonucleotide to said canine chromosome; and identifying said canine chromosomes by comparing said profile pattern of hybridization of each hybrid with a standard canine hybridization profile pattern.

In each method, differentiating or identifying, the oligonucleotide can be labeled in any detectable manner known in the art. In one embodiment, the oligonucleotide is labeled with biotin prior to hybridization with the canine chromosomes. After hybrids are formed, the biotin labeled oligonucleotide within the hybrids is detected by further labeling the oligonucleotide with fluorescent avidin (the avidin binds to the biotin) such as fluoro-avidin DN. Alternatively, the oligonucleotide can be labeled with a fluorescent marker prior to hybridization. Preferably, the oligonucleotide is labeled and fluorescently detected, either directly or indirectly (i.e. the fluorescent label is directly attached to the oligonucleotide or indirectly attached via another molecule such as biotin).

The invention also provides a method for differentiating canine chromosomes in a specimen which comprises:

contacting canine chromosomes in a specimen under hybridization conditions with a labeled repetitive probe, said probe capable of differentially hybridizing to canine chromosomes, so as to produce hybrids between said canine chromosomes and said labeled repetitive probe;

detecting the resulting hybrids by detecting the labeled repetitive probe present in the hybrids fluorescently;

determining for each hybrid a profile pattern of hybridization of said labeled repetitive probe to said canine chromosome; and differentiating said canine chromosomes by comparing said profile pattern of hybridization of each hybrid to profile patterns of the other hybrids.

Also provided is a method for identifying canine chromosomes in a specimen which comprises:

contacting canine chromosomes in a specimen under hybridization conditions with a repetitive probe, said probe capable of differentially hybridizing to canine chromosomes, so as to produce hybrids between said canine chromosomes and said repetitive probe;

detecting the resulting hybrids by detecting the labeled repetitive probe present in the hybrids fluorescently;

determining for each hybrid a profile pattern of hybridization of said repetitive probe to said canine chromosome; and identifying said canine chromosomes by comparing said profile pattern of hybridization of each hybrid with a standard canine hybridization profile pattern.

In each method, differentiating or identifying, the repetitive probe can be labeled in any fluorescently detectable manner known in the art. In one embodiment, the repetitive probe is labeled with biotin prior to hybridization with the canine chromosomes. After hybrids are formed, the biotin labeled repetitive probe within the hybrids is detected by further labeling the repetitive probe with fluorescent avidin (the avidin binds to the biotin) such as fluoro-avidin DN. Alternatively, the repetitive probe can be labeled with a fluorescent marker prior to hybridization. Fluorescent detection can be either direct or indirect (i.e. the fluorescent label is directly attached to the repetitive probe or indirectly attached via another molecule such as biotin).

In one embodiment the repetitive probe is the canid-specific repetitive probe having a nucleotide sequence which includes a sequence corresponding to SEQ ID NO:1. A canid-specific probe has a sequence which preferentially hybridizes to canid chromosomes as opposed to non-canid chromosomes. Alternatively, since the canine genome is double-stranded, the probe can have a nucleotide sequence which includes a sequence complementary to the sequence corresponding to SEQ ID NO:1. Additionally, the probe can comprise a fragment of either the sense or anti-sense strand, as long as the fragment remains capable of differentially hybridizing to canine chromosomes (see discussion above regarding identification of suitable fragments).

Preferably, the methods according to the subject invention are performed in situ. The term in situ means that the chromosomes are exposed from the cell nucleus without substantial disruption or relocation of the chromosomes with respect to each other and with the chromosomes being accessible to labeled probes.

The term in situ hybridization has reference to hybridization of a probe to a target that exists within a cytological or histological preparation or specimen. As a result of an in situ hybridization procedure, hybrids are produced between a probe and a target. This term in situ hybridization may be inclusive of denaturation and may also be inclusive of a hybrid or probe detection procedure which is practiced after in situ hybridization of a probe to a target. A specimen can be adhered as a layer upon a slide surface or provided as a suspension within a solution in a tube, and a specimen can, for example, comprise or contain individual chromosomes or chromosome regions which have been treated to maintain their morphology under, for example, denaturing conditions, or conditions such as typically exist during a flow cytometric analysis in a probe detection procedure. The term in situ hybridization may include use of a counterstain.

The term hybridizing conditions has general reference to the combinations of conditions that are employable in a given hybridization procedure to produce hybrids, such conditions typically involving controlled temperature, liquid phase, and contacting between a probe and a target.

The hybrids can be detected by various means, for example, with a fluorescent microscope, a flow cytometer, or the like. Detection involves irradiating the resulting specimen with energy which is at least sufficient to cause fluorophore groups present in the hybrhybrids to fluoresce while concurrently detecting the resulting fluorescent energy so produced. If the level of residual probe remaining unhybridized in the specimen interferes with detection, a separation step can be utilized to remove residual probe prior to detection.

The probe can be utilized in in situ hybridization procedures of the type that are commonly and conveniently carried out on specimens which have preliminarily been prepared and mounted on a slide, such as a slide comprised of glass or the like. For purposes of practicing such an in situ hybridization procedure, conventional slide preparation procedures can be employed, such as taught, for example, by Bosman et al. (1969) and Pardue (1969), and conventional in situ hybridization procedures can be employed, such as taught, for example, by Bhatt et al. (1988) and Hopman et al. (1987). For a discussion of fluorescent in situ hybridization (FISH) techniques, see generally U.S. Pat. Nos. 5,041,733 and 5,138,170 to Noguchi, PCT International Publication No. WO 9306245 to Bittner et al., Fan et al. (1990), and Rajcan-Separovic et al. (1993), the contents of each of which are hereby incorporated by reference.

It will be appreciated that any convenient contacting procedures and associated equipment can be employed. In the case where the specimen is uniformly deposited on an inert slide surface, the probe composition can be deposited upon and spread over such specimen surface. The amount used should be sufficient to achieve a complete wetting and contacting of such surface by such probe composition. The specimen is always preferably uniformly contacted with the treating probe composition. Next, the combination of the specimen and the treating probe composition that is in contact therewith are subjected to an incubation period. During this incubation period, the treating probe composition undergoes hybridization with the chromosomal DNA that is present in the specimen. The probe composition penetrates into and through such specimen and is capable of hybridizing with the chromosomal DNA so present to form hybrids. At the end of the incubation time period, the resulting specimen is subjected to a liquid washing procedure that is adapted to separate therefrom unreacted, residual treating probe composition. Advantageously, washing procedures similar to those known in the art of in situ hybridization can be used (for example, see Bhatt et al. (1988))

The invention also provides a recombinant plasmid designated pCfBE013/BH, deposited with the ATCC in *Escherichia coli* under Accession No. 69770. This recombinant plasmid contains the DNA encoding a suitable repetitive probe for use in the methods of the subject invention. The recombinant plasmid pCfBE013/BH was constructed by inserting the DNA encoding the repetitive probe of the subject invention into the BamHI site of plasmid vector pBR322. Therefore, the DNA encoding the repetitive probe of the subject invention can be obtained by cleaving recombinant plasmid pCfBE013/BH with the restriction endonuclease BamHI. The resulting BamHI restriction fragment encodes a repetitive probe for use in the methods of the subject invention. The construction of recombinant plasmids is done using conventional techniques, generally involving the use of restriction enzyme cleavage and ligation with DNA ligase (see U.S. Pat. No. 4,237,224 to Cohen and Boyer, the contents of which are hereby incorporated by reference; and Sambrook et al. (1989)).

Fluorescent in situ hybridization (FISH) with the pCfBE013/BH probe marks a majority of the canine chromosomes in a specific and unique manner. This probe is especially valuable in marking the smallest chromosomes (which are the most difficult to discriminate by G-banding).

The pattern of cytogenetic hybridization observed with the pCfBE013/BH probe differs in some important regards from the banding patterns observed by hybridizing the predominant human interspersed repeats (the Alu and L1 repetitive families) to human chromosomes. Hybridization with the Alu repeat generates fluorescent bands which provide a good match in localization, intensity, and resolution to R-banding of the human karyotype (Korenberg and Rykowski, 1988). Hybridization with the L1 repeat generates a fluorescing pattern which resembles (but with less resolution) G-banding (Korenberg and Rykowski, 1988). This differs from the pCfBE013/BH probe which labels a limited number of the autosomes. The autosomes which are labelled display hybridization only in scattered sites (predominantly euchromatic) rather than throughout the length of the chromosome arm. Thus, the pCfBE013/BH probe has a different chromosome hybridization pattern from human SINEs and LINEs.

Materials and Methods

Sequence analysis.

Plasmid DNA was purified using previously described methods (Hershfield and Swift, 1990). Sequencing was done using an automated sequencer (ABI). The GeneWorks computer package (IntelliGenetics, Mountain View, Calif.) was used to analyze sequences. Databank homology searches were performed using the NCBI server and the BLAST computer package (Altschul et al., 1990).

Southern blotting.

Genomic DNA was prepared as described (Hershfield et al., 1991) from blood samples from individual domestic dogs (*Canis familiaris*), C57BL mice (*Mus musculus*), cats (*Felis catus*), and humans (*Homo sapiens*). Ten microgram restriction digests were loaded in 1% agarose gels and electrophoresed in 1× TBE at 2 V/cm for 16–22 hours. Southern transfer was performed according to standard methods. The membranes were prehybridized for two hours at 42° C. in a buffer consisting of 5× SSC, 5× Denhardt's, 40% formamide, and 0.5% SDS. The membranes were hybridized overnight at 42° C. with 17.5 ng/ml biotinylated probe (Bionick nick translation kit, BRL, Gaithersburg, Md., U.S.A.) in a buffer consisting 5× SSC, 1× Denhardt's, 40% formamide, 0.5% SDS, and 5% dextran sulfate. Posthybridization washes were 2× SSC, 1% SDS (two times, five minutes each, room temperature), 0.1× SSC, 1% SDS (two times, 15 minutes each, 50° C.), and 1× SSC (four times, five minutes each, room temperature). Signal detection was performed using the protocols and reagents of a streptavidin-alkaline phosphatase chemiluminescent kit (Photogene, BRL, Gaithersburg, Md., U.S.A.) as described before (Hershfield et al., 1991; Hershfield et al., 1993). XAR film was exposed for seven to twenty-five minutes.

Fluorescence in situ hybridization (FISH).

Peripheral blood was collected in heparinized vacutainer tubes from a Belgian sheepdog. About 600 µl were incubated for 24–72 hours at 37° C. in 10 ml of RPMI 1640 supplemented to final concentrations of 15% of Chang A and B (GibcoBRL, Bethesda, Md. U.S.A.). 25 µg of PHA (Wellcome, UK) and 2 mg of pokeweed mitogen (GibcoBRL) were also added to the cultures. Thirty minutes prior to harvest, 0.15 µg of colcemid (GibcoBRL) and 100 µg/ml actinomycin-D were added to the lymphocyte cultures. Cells were pelleted and resuspended in 10 mls of a hypotonic solution of 0.075M KCl/NaCitrate. Cells were gently fixed and washed in three changes of 5 ml of prechilled methanol-acetic acid (3:1). The swollen and fixed cells were then dropped onto precleaned cold, wet slides, heated, and air-dried. Spread preparations on slides were treated with RNAase (200 µg/ml) for 30 minutes at 37° C. followed by denaturation in 2× SSC at 80° C. for 5–15 minutes. Chromosome spreads were then hybridized in a mix consisting of 2.5× SSC, 0.05% Triton X-100, 10% dextran sulfate, 125 µg/ml of sonicated herring sperm carrier DNA, and 5 ng/µl biotinylated pCfBE013/BH probe (nick-translated with Bio-16-dUTP (Enzo, New York, N.Y. U.S.A.)). Unlabelled sonicated dog DNA at 125 µg/ml was also used either in a separate prehybridization step or by adding it to the hybridization cocktail. Slides were rinsed in 2× SSC at 60° C. (2×10 minutes) followed by rinses in 1× SSC, 0.1× SSC (60° C.; 2×10 minutes) and 0.1× SSC at room temperature (10 minutes). Slides were then transferred to 0.1M phosphate buffered saline (pH 7.2, room temperature; 2×10 minutes). The biotinylated probe was detected by incubation with fluoro-avidin DN (Sigma, St. Louis, Mo. U.S.A.) followed by a repeated series (2–3 times) of sequential incubations with biotinylated goat-anti-avidin D (Sigma) (1:200) and fluoro-avidin DN to intensify the fluorescent signal. Chromosomes were counterstained with propidium iodide. Chromosome sets were viewed on a Zeiss IM 35 or Olympus BX50 with a BioRad MRC-1000 confocal laser scanning microscope using a 100× oil immersion NA 1.4 objective. A rhodamine filter cube was used to visualize the counterstained chromosomes and a FITC filter cube was used to visualize the hybridization signal.

Results

The middle repetitive probe pCfBE013/BH was selected on the basis of hybridization signal intensity from a canine genomic minilibrary enriched for inserts which could detect polymorphisms (Hershfield et al., 1993). The first 124 bp were homologous to a previously described canid-specific SINE element unrelated to evolutionarily conserved SINEs such as Alu (Minnick et al., 1992). The extent of homology of the first 124 bp was 90%, and the homologous region was followed by a microsatellite motif (see SEQ ID NO:1). The remaining 590 bp did not have significant homology to sequences in the NCBI databanks (maximum Poisson score= 0.30).

When the probe was hybridized to canine genomic DNA digested with a variety of restriction enzymes, smears of hybridization characteristic of interspersed sequences were noted.

Following in situ hybridization of the pCfBE013/BH probe to canine mitotic metaphase chromosome sets, one to two pairs of hybridization signal were found on most chromosomes (FIG. 1). About 25–30% of the autosomes were labelled weakly or not at all by the probe. Although some of the sites of hybridization seem to be located in the centromeric and telomeric regions, many of the sites appear dispersed on the euchromatic arms. Thus, the probe displays specificity in marking the canine autosomes at two levels: certain chromosome pairs have hybridizing sites while others do not, and the pattern of marking appears unique to a particular chromosome pair or to a discrete and limited subset of chromosomes. Characteristic hybridization patterns for nine representative autosomes are presented in FIG. 1. These hybridization patterns were reproducible in over 30 examined spreads from three animals. The observed signal is due to specific hybridization to the canine chromosomes since no signal was detected from hybridizations to chromosome spreads from mouse or man using the same techniques and reagents.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Altschul, S. F. et al., Basic local alignment search tool. J Mol Biol 215:403–410 (1990).

Amariglio, E. N. et al., Identity of rearranged LINE/c-MYC junction sequences specific for the canine transmissible venereal tumor. Proc Natl Acad Sci U.S.A. 88:8136–8139 (1991).

Bhatt, B. et al., Nucl Acids Res 16:3951–3961 (1988).

Bosman, F. T. et al., Genetica 5:425–433 (1975).

Fan, Y. S. et al., Proc Natl Acad Sci U.S.A. 87:6223–6227 (1990).

Hershfield, B. and Swift, H., Characterization of a tandemly repeated DNA from the fleshly Sarcophaga bullata. Chromosoma 99:125–130 (1990).

Hershfield, B. et al., Organization and transcription of canine (CAC)n sequences. J Hered 82:251–254 (1991).

Hershfield, B. et al., Cloning of a polymorphic canine genetic marker which maps to human chromosome 9. Anim Genet 24:293–295 (1993).

Hino, O. et al., Universal mapping probes and the origin of human chromosome 3. Proc Natl Acad Sci USA 90:730–734 (1993).

Hopman, A. H. N. et al., Exp Cell Res 169:357–368 (1987).

Katzir, N. et al., "Retroposon" insertion into the cellular oncogene c-myc in canine transmissible venereal tumor. Proc Natl Acad Sci USA 82:1054–1058 (1985).

Korenberg, J. R. and Rykowski, M. C. Human genome organization: Alu, Lines, and the molecular structure of metaphase chromosome bands. Cell 53:391–400 (1988).

Lin, C. C. et al., New evidence for tandem chromosome fusions in the karyotypic evolution of Asian muntjacs. Chromosoma 101:19–24 (1991).

Manolache, M. et al., Banding analysis of the somatic chromosomes of the domestic dog (*Canis familiaris*). Can J Genet Cytol 18:513–518 (1976).

Minnick, M.F. et al., A highly repetitive DNA sequence possibly unique to canids. Gene 110:235–238 (1992).

Modi, W. S. et al., Chromosomal localization of satellite DNA sequences among 22 species of felids and canids (Carnivora). Cytogenet Cell Genet 48:208–213 (1988).

Ostrander, E. A. et al., Identification and characterization of dinucleotide repeat (CA) n markers for genetic mapping in dog. Genomics 16:207–213 (1993).

Pardue, G., Proc Natl Acad Sci USA 64:600 (1969).

Pathak, S. et al., Heterochromatin, synaptonemal complex, and NOR activity in the somatic and germ cells of a male domestic dog, *Canis familiaris* (Mammalia, Canidae). Cytogenet Cell Genet 34:112–118 (1982).

Rajcan-Separovic, E. and Sabour, M. P. Fluorescence in situ hybridization of bovine Alu-like sequences to bovine and ovine chromosomes. Genome 36:984–986 (1993).

Sambrook et al., *Molecular Cloning: A Laboratory Manual*, Cold Spring Harbor Laboratory Press, Cold Spring Harbor, N.Y. (1989).

Selden, J. R. et al., The Giemsa Banding Pattern of the Canine Karyotype. Cytogenetics and Cell Genetics 15:380–387 (1975).

Stone, D. M. et al., The Giemsa banding pattern of canine chromosomes, using a cell synchronization technique. Genome 34:407–412 (1991).

Wayne, R. K. et al., Chromosomal evolution of the Canidae. I. Species with high diploid numbers. Cytogenet Cell Genet 44:123–133 (1987a).

Wayne, R. K. et al., Chromosomal evolution of the Canidae. II. Divergence from the primitive carnivore karyotype. Cytogenet Cell Genet 44:134–141 (1987b).

Yasue, H. et al., Uneven distribution of short interspersed repetitive sequence, PRE-1, on swine chromosomes. Cell Struct Funct 16:475–479 (1991).

---

What is claimed is:

1. An isolated oligonucleotide consisting of SEQ ID NO:1 or a sequence fully complementary to SEQ ID NO:1.

2. The isolated oligonucleotide of claim 1 labeled with a detectable marker.

3. The isolated oligonucleotide of claim 2 wherein said detectable marker comprises biotin.

4. The isolated oligonucleotide of claim 2 wherein said detectable marker comprises a fluorescent marker.

5. The isolated oligonucleotide of claim 1 wherein said oligonucleotide comprises DNA.

6. The isolated oligonucleotide of claim 1 wherein said oligonucleotide comprises RNA.

7. A composition comprising the isolated oligonucleotide of claim 1 and at least one other oligonucleotide capable of differentially hybridizing to canine chromosomes.

8. A fragment of the isolated oligonucleotide of claim 1 capable of differentially hybridizing to canine chromosomes.

9. A composition comprising the fragment of claim 8 and at least one other oligonucleotide capable of differentially hybridizing to canine chromosomes.

10. A method for differentiating canine chromosomes in a specimen which comprises:

contacting canine chromosomes in a specimen under hybridizing conditions with a labeled isolated oligonucleotide of claim 1 so as to produce hybrids between said canine chromosomes and the labeled oligonucleotide;

detecting the hybrids by detecting the labeled oligonucleotide present in the hybrids;

determining for each hybrid a profile pattern of hybridization of said labeled oligonucleotide to said canine chromosome; and differentiating said canine chromosomes by comparing said profile pattern of hybridization of each hybrid to profile patterns of the other hybrids.

11. The method of claim 10 wherein said labeled isolated oligonucleotide comprises said isolated oligonucleotide labeled with biotin.

12. The method of claim 11 wherein said biotin labeled oligonucleotide present in said hybrids is detected fluorescently.

13. The method of claim 10 wherein said labeled isolated oligonucleotide comprises said isolated oligonucteotide labeled with a fluorescent marker.

14. The method of claim 10 wherein said labeled oligonucleotide present in said hybrids is detected fluorescently.

15. A method for identifying canine chromosomes in a specimen which comprises:

contacting canine chromosomes in a specimen under hybridizing conditions with a labeled isolated oligonucleotide of claim 1 so as to produce hybrids between said canine chromosomes and the labeled oligonucleotide;

detecting the hybrids by detecting the labeled oligonucleotide present in the hybrids;

determining for each hybrid a profile pattern of hybridization of said labeled oligonucleotide to said canine chromosome; and identifying said canine chromosomes by comparing said profile pattern of hybridization of each hybrid with a standard canine hybridization profile pattern.

16. The method of claim 15 wherein said labeled isolated oligonucleotide comprises said isolated oligonucleotide labeled with biotin.

17. The method of claim 16 wherein said biotin labeled oligonucleotide present in said hybrids is detected fluorescently.

18. The method of claim 15 wherein said labeled isolated oligonucleotide comprises said isolated oligonucleotide labeled with a fluorescent marker.

19. The method of claim 15 wherein said labeled oligonucleotide present in said hybrids is detected fluorescently.

20. A recombinant plasmid designated pCfBE013/BH which comprises a BamHI restriction fragment of about 737 bp, deposited with the A.T.C.C. in *Escherichia coli* under A.T.C.C. Accession No. 69770.

21. An isolated Bam HI restriction fragment comprising about 737 bp from the recombinant plasmid designated pCfBE013/BH, said recombinant plasmid deposited with the A.T.C.C. in *Escherichia coli* under A.T.C.C. Accession No. 69770.

* * * * *

UNITED STATES PATENT AND TRADEMARK OFFICE
CERTIFICATE OF CORRECTION

PATENT NO. : 5,648,216
DATED : July 15, 1997
INVENTOR(S) : Hershfield et al.

It is certified that error appears in the above-indentified patent and that said Letters Patent is hereby corrected as shown below:

TITLE PAGE:

Under heading [73] Assignee, the following text should be added: --; The University of Tennessee Research Corporation, Knoxville, T.N.--

Signed and Sealed this

Twenty-eighth Day of October, 1997

Attest:

BRUCE LEHMAN

Attesting Officer

Commissioner of Patents and Trademarks